US00PP18328P2

(12) United States Plant Patent
Reardon

(10) Patent No.: US PP18,328 P2
(45) Date of Patent: Dec. 18, 2007

(54) ***RHODODENDRON* PLANT NAMED 'PJM PINK DELIGHT'**

(50) Latin Name: ***Rhododendron* sp.**
Varietal Denomination: PJM Pink Delight

(75) Inventor: Michael D. Reardon, Boring, OR (US)

(73) Assignee: Reardon Nursery, Inc., Boring, OR (US)

( * ) Notice: Subject to any disclaimer, the term of this patent is extended or adjusted under 35 U.S.C. 154(b) by 18 days.

(21) Appl. No.: 11/442,074

(22) Filed: May 25, 2006

(51) Int. Cl.
*A01H 5/00* (2006.01)

(52) U.S. Cl. ..... Plt./238
(58) Field of Classification Search ..... Plt./238
See application file for complete search history.

*Primary Examiner*—Kent Bell
*Assistant Examiner*—Annette H Para
(74) *Attorney, Agent, or Firm*—Klarquist Sparkman, LLP

(57) ABSTRACT

A new and distinct cultivar of *Rhododendron* plant characterized by its pink lavender flowers in terminal rounded trusses, deep mahogany purple winter leaves, and upright, dense growth habit.

1 Drawing Sheet

Botanical classification: *Rhododendron* sp.
Variety nomination: 'PJM Pink Delight'.
Parentage: Chance mutation of *Rhododendron* 'PJM'.

The present invention relates to a new and distinct cultivar of an evergreen shrub of the genus, *Rhododendron,* and given the name 'PJM Pink Delight'. The genus *Rhododendron* is of the family Ericaceae.

The new cultivar was found in a cultivated area of a nursery in Boring, Oreg., by Michael Reardon as a chance mutation of *Rhododendron* 'PJM', an unpatented plant. The original plant of the new variety was first noticed by the inventor because of its pink lavender flowers. These flowers were very different in color from the purple blue lavender color of the flowers of 'PMJ' *Rhododendron* plants growing in the same group of plants containing the original 'PMJ Pink Delight' plant. Apart from the flower colors, the inventor observed no other differences between the original 'PJM Pink Delight' plant and these 'PJM' *Rhododendron* plants. The original plant of the new variety and all of these other plants growing in the group of plants with the original plant of the new variety when the original plant of the new variety was discovered had all been purchased as tissue culture reproduced plants of the 'PJM' variety. As these plants grew, the original plant of my new variety exhibited its distinctive characteristics and thus, even though purchased as a tissue culture reproduced plant of the 'PJM' variety, the original plant of my new variety was not of the 'PJM' variety, but instead is a new variety of plant. The inventor checked with the source of these tissue culture plants and was informed that the source was not aware of any other plants, apart from the original 'PJM Pink Delight' plant discovered by the inventor, that had this property. This confirmed that the new plant is indeed a chance mutation.

*Rhododendron* 'PJM' is well known for its upright, dense growth habit, strong stems, deep mahogany purple winter leaves, profuse spring flowering in terminal rounded trusses, purple blue lavender flowers, and early bloom time. It is widely adaptable and easy to grow.

This new cultivar 'PJM Pink Delight' has all of these good qualities, but is uniquely different in its flower color. The flowers of *Rhododendron* 'PJM Pink Delight' are pink lavender flowers rather than the purple blue lavender flower color of *Rhododendron* 'PJM'.

Asexual propagation by cuttings in Boring, Oreg., first asexual propagation having been accomplished in the Fall of 2000 or early in 2001, shows that the foregoing characteristics and distinctions come true to form and are established and transmitted through succeeding propagations. The present invention has not been evaluated under all possible environmental conditions. The phenotype may vary with changes in environment without a change in the genotype of the plant.

BRIEF DESCRIPTION OF THE DRAWING

FIG. 1 shows a mature 3 year old 'PMJ Pink Delight' plant growing in a 2 gallon container in full bloom in April 2006 in Boring, Oreg.

FIG. 2 shows a close up of a flowering branch of this plant.

DETAILED PLANT DESCRIPTION

The following is a detailed description of the new cultivar based on observations taken in early April of 2006 of a three-year-old specimen grown in a 2 gallon container in full sun in Boring, Oreg. Boring, Oreg. is in USDA hardiness zone 7. The color descriptions are all based on The Royal Horticultural Society Colour Chart.

Plant:
- *Type.*—Evergreen shrub.
- *Hardiness.*—Only grown in Boring, Oreg., hardiness zone 7, expected to be hardy in USDA Zones 4 to 8.
- *Size.*—35 cm tall and 40 cm wide. Mature plants have not yet been observed.
- *Growth habit.*—Upright, dense, rounded.

Stem:
- *Type.*—Woody.
- *Size.*—Trunk base is 1.8 cm at 1 cm above the ground.
- *Surface.*—Young stems are densely scaled, 2 year and older stems are smooth.
- *Vigor.*—Excellent, observed to grow with the same vigor of 'PMJ' plants growing in the same area.
- *Rooting.*—From current season's wood takes 120 days to root.

*Color.*—Young, 1 year old stems are Brown 200A, 2 year and older stems are grey brown, between Grey Brown 199D and Greyed Green 197D.

Leaf:

*Type.*—Simple.

*Shape.*—Elliptic, often convex.

*Arrangement.*—Alternate.

*Margins.*—Entire.

*Apex.*—Acute.

*Base.*—Cuneate.

*Venation.*—Pinnate.

*Blade length.*—Exemplary leaf, about 5.5 cm.

*Width.*—Exemplary leaf, about 2.7 cm.

*Texture.*—Leathery.

*Surface.*—Glossy and scaly on top side; dense, rust colored, scaly indumentum on bottom side, Grey Brown 199A.

*Petiole description.*—5 mm long and 1 mm wide, scaly, Greyed Orange 177A on topside and Greyed Orange 174A on bottom side.

*Color.*—Topside — deep mahogany-purple November to April, with bloom they lighten to between Yellow Green 147A and Brown 200A. These lighten to Yellow Green 147A on summer leaves. Bottom side — All seasons, Yellow Green 147C heavily tinted Grey Brown 199A, vein Greyed Orange 174A.

Inflorescence:

*Type.*—Terminal congested raceme (trusses).

*Number of trusses per plant.*—60 to 83.

*Number of flowers per truss.*—5 to 14.

*Dimensions of a truss.*—Exemplary truss, 8 cm wide by 3.5 cm deep.

*Peduncle description.*—Under the bracts, exemplary peduncle 2 mm long and 1 mm diameter, scaly, Yellow 11B.

*Pedicel description.*—Exemplary, 9 to 10.5 cm long, 1 mm diameter, scaly, Yellow 2D.

*Bloom period.*—Mid March through April in Boring, Oreg.

Flower bud:

*Size.*—Exemplary bud, 6 mm diameter and 12 mm long.

*Description.*—Ovoid.

*Color.*—Purple 77B.

Flower:

*Type.*—Perfect, irregular.

*Corolla description.*—Exemplary corolla, 2.2 cm deep and 4 cm wide overall, openly funnel form, tube 8 mm deep and 15 mm wide at the top, 5 lobed, lobes broadly ovate, undulate, overlapping at the base, obtuse, 16 mm long and 10 mm wide, glabrous inside, pubescent backside.

*Corolla color.*—Pink-Lavender 77C to 77D inside and out with Purple 78A spotting inside below the upper most lobe.

*Calyx.*—None.

*Stamen description.*—10, Exemplary stamen 17 mm long, filaments 17 mm long and less than 1 mm diameter, pubescent on bottom ¼, White 155D, stamen 1.5 mm long, Greyed Yellow 161D, pollen sparse, Greyed Yellow 161D.

*Pistil description.*—Exemplary pistil, 22 mm long, ovary 3 mm long and 1.7 mm wide, Yellow Green 147C, style 18 mm long and 0.5 mm wide, Red Purple 65C, stigma Red Purple 67A.

*Fragrance.*—None.

Fruit: None observed to be formed.

Seed: None observed.

Pest and disease tolerance: Plants of *Rhododendron* 'PJM Pink Delight' have not been observed to have any special pest or disease resistance.

COMPARISONS TO SIMILAR VARIETIES

Compared to the parent plant, *Rhododendron* 'PJM', the new variety has lighter, pinker flowers.

Compared to *Rhododendron* 'Olga Mezitt', unpatented, the new variety has stronger stems which hold up better in climates with snow.

Compared to *Rhododendron* 'Weston's Aglo', unpatented, the new variety blooms 2 weeks earlier, grows taller, and has a dense rather than open habit.

I claim:

1. A new and distinct *Rhododendron* plant as herein illustrated and described.

* * * * *

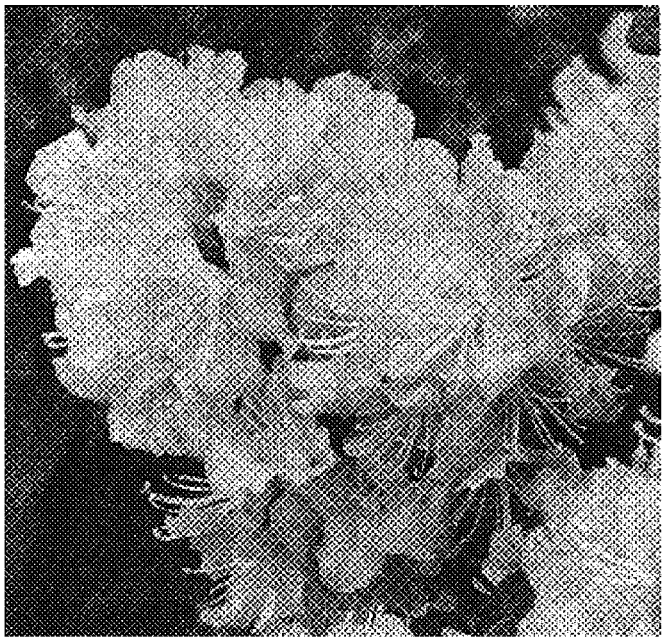

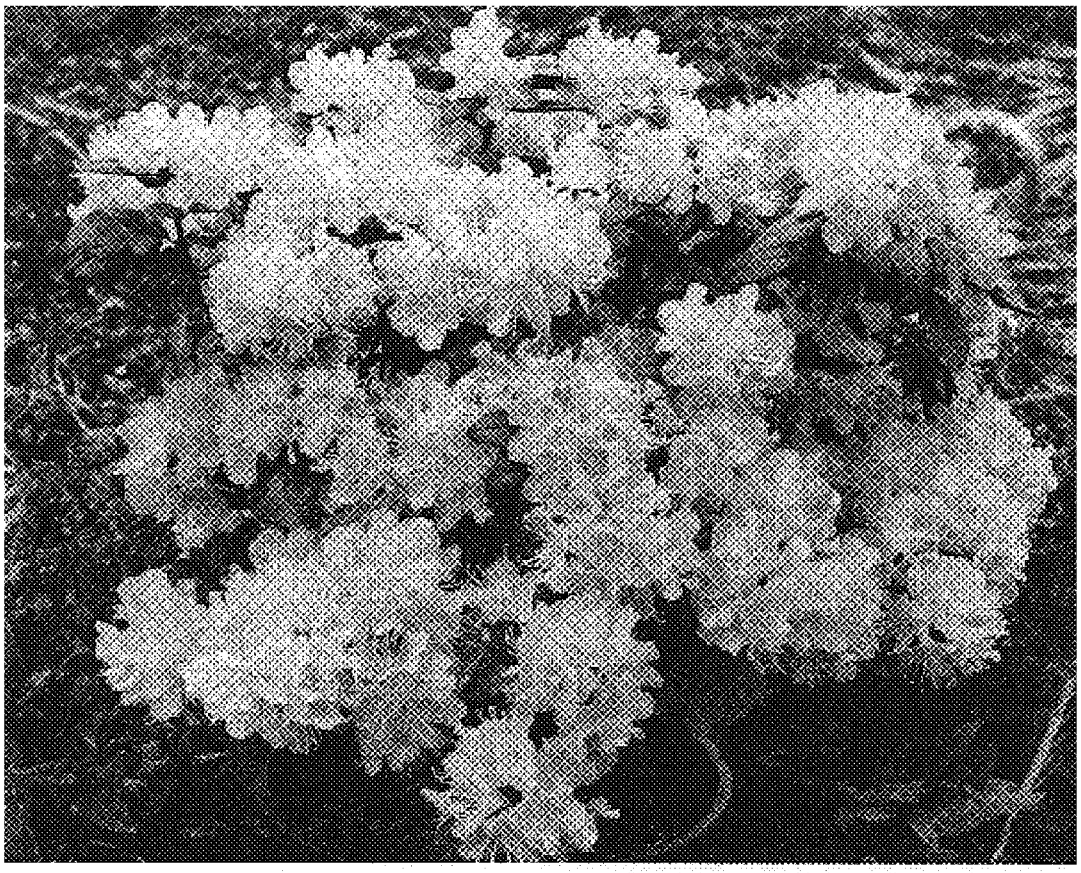
Figure 1 above, Figure 2 below